(12) United States Patent
Marino et al.

(10) Patent No.: US 6,303,577 B1
(45) Date of Patent: Oct. 16, 2001

(54) USE OF A PEPTIDE COMPOUND IN THE TREATMENT OF SYSTEMIC LUPUS ERYTHEMATOSUS

(75) Inventors: Maria Marino, Caserta; Maria Rossi, Portici; Giorgio Fassina, Milan, all of (IT)

(73) Assignee: Tecnogen S.C.p.A., Piana di Monte Verna (IT)

( * ) Notice: Subject to any disclaimer, the term of this patent is extended or adjusted under 35 U.S.C. 154(b) by 0 days.

(21) Appl. No.: 09/304,052

(22) Filed: May 4, 1999

(30) Foreign Application Priority Data

May 21, 1998 (EP) .................................................. 98830310

(51) Int. Cl.$^7$ .................................................. A61K 38/00
(52) U.S. Cl. .................. 514/17; 514/2; 260/112; 260/112.5
(58) Field of Search ................ 514/17, 2; 260/112, 260/112.5

(56) References Cited

FOREIGN PATENT DOCUMENTS

WO 97/16410    5/1997    (WO) .

OTHER PUBLICATIONS

Pharm. Res. 10(9), 1268–73, 1993.*

Encyclopedia Britannica Online.*

Giorgio Fassina, et al., "Protein A Mimetic Peptide Ligand for Affinity Purification of Antibodies," Journal of Molecular Recognition, vol. 9, (1996), pp. 564–569.

* cited by examiner

*Primary Examiner*—Jean C. Witz
*Assistant Examiner*—Brett Ozga
(74) *Attorney, Agent, or Firm*—Oblon, Spivak, McClelland, Maier & Neustadt, P.C.

(57) ABSTRACT

Use of a peptide compound of formula $$(H_2N-X_1-Thr-X_2-CO)_n-R \qquad (I)$$

wherein $X_1$, $X_2$, n and R have the meanings stated in the description for preparing a pharmaceutical composition useful in the treatment of Systemic Lupus Erythematosus.

43 Claims, No Drawings

USE OF A PEPTIDE COMPOUND IN THE TREATMENT OF SYSTEMIC LUPUS ERYTHEMATOSUS

This application is based on European Patent Application No. 98830310.3 filed on May 21, 1998, the content of which is incorporated hereinto by reference.

This invention relates to the use of a peptide compound for preparing a pharmaceutical composition useful in the treatment of Systemic Lupus Erythematosus as well as a method of treating a patient suffering from Systemic Lupus Erythematosus.

EP-A-752 425 discloses a peptide compound of formula

wherein $X_1$ and $X_2$, different one another, are an amino acid residue of arginina or tyrosine in configuration L or D, wherein the hydroxy group of threonine and tyrosine and the guanidine moiety of arginine may be protected by a compound conventionally used in peptide chemistry for protecting the hydroxy group and the guanidine moiety, respectively, n is 1, 2, 3 or 4, and R, when n is 2, 3 or 4 is a group suitable for forming a dimer, trimer or tetramer, while, when n is 1, R is OH, a single amino acid residue, or a peptide chain comprising up to 7 amino acid residues, useful as a ligand of immunoglobulins.

PCT/EP97/07143 discloses a pharmaceutical composition containing a biologically effective amount of a peptide compound of formula

wherein $X_1$ and $X_2$ have the above mentioned meanings, n is 2, 3 or 4,

R is a group capable to form a dimeric, trimeric, and respectively tetrameric peptide, and at least a pharmaceutically acceptable inert ingredient.

These compounds proved to be particularly useful in vivo in the treatment of allergic reactions.

The content of EP-A-752 425 and PCT/EP97/07143 is incorporated herein by reference.

Systemic Lupus Erythematosus (SLE) is a chronic, remitting and relapsing, multisystem autoimmune disease that affects predominantly women, with an incidence 1:700 in women between 20 and 60 years old, while the female:male ratio is 10:1.

The main clinical syndrome comprises skin rashes, arthritis, and glomerulonephritis. Hemolytic anemia, thrombocytopenia, and central nervous system involvement are also common.

Many different antibodies are found in patients with SLE. The most frequent are antinuclear, particularly anti-DNA antibodies and anti-ribonucleoproteins, -histones, -nucleolar antigens, -erythrocytes, -platelets antibodies.

So far, Systemic Lupus Erythematosus has been treated with aspirin and other anti-inflammatory drugs, or with antimalarial drugs.

Further, severe disease with vasculitis involvement of nervous system and renal damage, requires immediate corticosteroid therapy in combination with immunosuppressives as methotrexate and cyclosporine.

These drugs, however, may cause serious side effects. The most common side effects of aspirin are liver damages, while antimalarial drugs cause nausea and vomiting. Common side effects of the cortisone-like drugs include weight gain, insomnia and depression, while administration of corticosteroids over a long period of time may lead to osteoporosis and cataracts.

Furthermore, the immunosuppressive drugs can interfere with the formation of blood cells, increase the development of infections, and cause severe renal damages.

Now it has been found that the peptide compound of formula

where $X_1$, $X_2$, R and n have the meanings given herein below, is useful in the treatment of Systemic Lupus Erythematosus.

Therefore, in a first aspect this invention relates to the use of a peptide compound of formula

where $X_1$ and $X_2$ different one another, are an amino acid residue of tyrosine and arginine, in L or D configuration, wherein the hydroxy group of threonine and the guanidine moiety of arginine may be protected by a compound conventionally used in peptide chemistry for protecting the hydroxy group and the guanidine moiety, respectively, n is 2, 3, or 4, and R is a group able to form a dimeric, trimeric, and respectively tetrameric peptide, for preparing a pharmaceutical composition useful in the treatment of Systemic Lupus Erythematosus.

In a second aspect this invention relates to a method of treating a patient suffering from Systemic Lupus Erythematosus, said method comprising administering to a patient in need thereof an effective amount of a peptide compound of formula

where $X_1$, $X_2$, R and n have the meanings given above in connection with the first aspect of this invention.

Preferably n is 4.

Each amino acid of the compound of formula (I) can have L or D configuration.

In the present description and in the claims, the terms "dimer" "trimer" and "tetramer" intend to mean peptides comprising two, three and respectively four sequences $H_2N$—$X_1$-Thr-$X_2$—CO— where $X_1$ and $X_2$ have the above mentioned meaning.

A typical example of a suitable group for forming a dimer (n=2) is a lysine residue. A typical example of a suitable group for forming a trimer (n=3) is a dipeptide lysil-lysine of formula Lys-Lys. Typical examples of suitable groups for forming a tetramer (n=4) are a branched tripeptide of formula Lys-Lys($\epsilon$Lys) and a branched tetrapeptide of formula Gly-Lys-Lys($\epsilon$Lys).

A typical example of a tetramer of formula (I) has the following formula

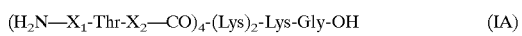

where $X_1$ and $X_2$ have the above mentioned meanings, and wherein the hydroxy group of threonine and tyrosine and the guanidine moiety of arginine may be protected by a compound conventionally used in peptide chemistry for protecting the hydroxy group and the guanidine moiety, respectively.

Many groups useful for protecting the hydroxy group are reported in the literature (Grant G. A. "Synthetic peptides: a user's guide", Freeman, N.Y., 1992).

Typical examples of said protecting groups are the ter-butyl (tBu) (La Joie, G. Crivici, A., Adamson, J. G. et al., "Synthesis", 571–572, 1990) and the benzyl group (Yojima. "Tetrahedron", 44, 805–819, 1988).

Many groups useful for protecting the guanidine moiety of arginine are also known from the literature (Grant G. A. "Synthetic peptides: a user's guide", Freeman, N.Y., 1992).

Typical examples of said protecting groups are: 2,2,5,7,8-pen-tamethylcroman-6-sulphonyl(Pmc) and 4-methoxy-2,3,6-trimethylbenzene (Mtr) (Ramage & Green, "Tetrahedron Letters", 28, 2287, 1987); Fujino et al. "Chem. Pharm. Bull.", 29, 2825, 1981).

Specific examples of compound of formula (I) are

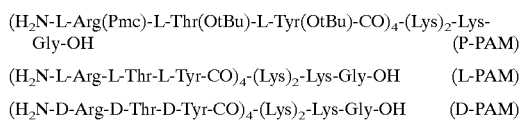

| | |
|---|---|
| ($H_2$N-L-Arg(Pmc)-L-Thr(OtBu)-L-Tyr(OtBu)-CO)$_4$-(Lys)$_2$-Lys-Gly-OH | (P-PAM) |
| ($H_2$N-L-Arg-L-Thr-L-Tyr-CO)$_4$-(Lys)$_2$-Lys-Gly-OH | (L-PAM) |
| ($H_2$N-D-Arg-D-Thr-D-Tyr-CO)$_4$-(Lys)$_2$-Lys-Gly-OH | (D-PAM) |

As shown in more details in the following examples, the peptide compounds of formula (I) proved to be active in an in vivo test on mice developing Systemic Lupus Erythematosus. More particularly, they proved to decrease the death rate of treated animals, and to reduce the damage on the kidneys caused by the disease.

Additionally, the peptide compounds of formula (I), proved to be well tolerated and devoid of immunogenic properties in mouse acute toxicity tests, either by oral or by intravenous administration.

Preferably, the pharmaceutical compositions according to this invention are prepared in a suitable dosage form comprising an effective dose of at least one peptide compound of formula (I) and at least one pharmaceutically acceptable inert ingredient.

Example of suitable dosage forms are pills, capsules, cover pills, granules, solutions and syrups for oral administration, unguents and plasters for topic administration; suppositories for rectal administration and sterile solutions for injectable, inhalation and ophthalmic administration.

The dosage forms may also contain other conventional ingredients like preservatives, stabilizers, surface-active agents, buffers, salts to regulate osmotic pressure, emulsifying agents, sweeteners, dyes, flavours and the like.

When required by particular therapies, the pharmaceutical composition of this invention may contain other active pharmacological ingredients whose concomitant administration is therapeutically useful.

The amount of a peptide compound of formula (I) in a pharmaceutical composition of this invention may vary in a rather wide range depending on known factors such as, for example, the type of disease to be treated, the severity of the disease, the body weight of patient, the dosage form, the chosen route of administration, the number of dosage forms administrated daily and the efficacy of the chosen peptide compound of formula (I).

Typically, the amount of a peptide compound of formula (I) in a pharmaceutical composition of this invention will be such as to assure an administration level of from 1 to 200 mg/Kg/day, preferably of from 2 to 50 mg/Kg/day.

The dosage forms of the pharmaceutical composition of this invention can be prepared according to techniques which are known to the pharmaceutical chemist and comprise procedures such as mixing, granulation, compression, dissolution, sterilization and the like.

The present invention is further described by the following Examples which are given for illustrative purposes only and should not be construed as a limitation of the invention.

EXAMPLE 1

Stability to Proteolytic Enzymes

The stability of the peptide compounds of formula (I) to proteolytic attack by proteases has been evaluated by High Performance Liquid Chromatography (HPLC).

Mouse sera were obtained by cutting a small section off tip of tail and collecting some blood drops. After collection, blood was incubated for 1 hour at 37° C. and then serum was removed from the clot by centrifugation at 1200 g for 20' at 4° C. Various amounts of peptide compounds of formula (I) were added to 50 μl of serum and the mixture was incubated at 37° C. for different periods of time. Afterwards, 2 μl of the reaction mixture were added to 50 μl of 0.1 M acetic acid in order to elute the peptide compound from serum immunoglobulins. Samples were then stored at −80° C. until use.

Analysis of samples was carried out on an Aquapore RP-8 column (30×2.1 mm I.D.), eluting the equilibrated column at a flow rate of 0.5 ml/min with a linear gradient of 0.1% trifluoracetic acid buffer containing increasing acetonitrile concentration from 5% to 60% in 35'. Elution was monitored by absorbance at 225 nm. The results are shown in Table 1.

TABLE 1

| | (%) Stability | | | | |
|---|---|---|---|---|---|
| | Incubation time (minutes) | | | | |
| Peptides | 0 | 5 | 20 | 40 | 60 |
| D-PAM | 100 | 83 | 73 | 68 | 63 |
| L-PAM | 100 | 57 | 31 | 19 | 12 |

Data reported in Table 1 show that D-PAM resulted more stable to proteolytic attack than L-PAM.

EXAMPLE 2

Immunogenicity

The ability of the peptide compounds of formula (I) to evoke an antibody response has been evaluated by immunizing two groups of four Balb/c mice with 100 μg of D-PAM or L-PAM respectively by i.p. injection. After the first immunization, the same immunogen was administered for two subsequent boosts, blood samples were collected from each animal for monitoring antibody titers by an ELISA assay as follow.

Polystyrene microtiter plates (Falcon Cat. No 3912) were coated with a 50 μg/ml D-PAM and L-PAM conjugated to BSA (100 μl/well) in 0.1 M sodium carbonate buffer (pH 8.5) and incubated over night at 4° C. After washing the microtiter plates ten times with a 50 mM phosphate, 150 mM NaCl pH 7.2 buffer (PBS), the wells were saturated with 200 μl of PBS containing bovine serum albumin (BSA, Sigma Cat. No A-9418) for 1 hour at 37° C., to block the uncoated plastic surface. Plates were then washed again with PBS containing 0.05% Tween 20 (PBS-T), and filled with samples (100 μl/well) previously diluted with PBS-T containing 1% BSA (PBS-T-B). After incubation for 1 hour at 37° C. and subsequent washing, wells were filled with 100 µl of horseradish peroxidase labeled sheep anti-mouse immunoglobulin lin F (ab')$_2$-specific (Sigma, Cat. No A-7282) solution diluted 1000 fold with PBS-T-B. The plates were then left to stand for 1 hour at 37° C., washed ten times and then filled with 150 µl of 2,2-Azino-di-[3-ethylbenzthiazoline sulfonate] (ABTS) chromogenic substrate solution freshly prepared according to protocols from the manufacturer (Boehringer Mannheim Cat. No 1112422). The color was allowed to develop for 30' and absorbances were read at 405 nm with an ELISA plate reader (Labsystems Multiskan Bichromatic). Preimmune serum has been used as control. The results are shown in Table 2.

TABLE 2

| Peptides | | Antibody titer (A 405) |
|---|---|---|
| L-PAM | Preimmune | 0.462 |
|  | Immune | 0.412 |
| D-PAM | Preimmune | 0.663 |
|  | Immune | 0.524 |

Data reported in Table 2 show that L-PAM and D-PAM are not able to produce an antibody response even in the susceptible mouse strain Balb/c.

EXAMPLE 3

Anti- human Systemic Lupus Erythematosus activity in vivo

In vivo studies on the activity of the peptide compounds of formula (I) were carried out by using an experimental animal model of human Systemic Lupus Erythematosus. MRL/Ipr, NZB/NZW or BXSB denote mouse strains that spontaneously develop an autoimmune syndrome having notable similarities to human Systemic Lupus Erythematosus. The MRL-Ipr/Ipr strain is homozigotic for Ipr gene. The lpr mutation causes functional defects in the Fas Ag. Fas belongs to the TNF receptor family and mediates apoptosis (Watanabe-Fukunaga, R. et al., "Nature", 356, 314, 1992; Itoh, N., et al., "Cell", 66, 233, 1991; Murphy, E. D., "Immunological defects in Laboratory Animals", 2, 143, 1981; Steinberg, A. D., "Semin. Immunol.", 6, 55, 1994). Autoimmune disease in MRL/Ipr mice is characterized by autoantibody production, vasculitis, arthritis, and glomerulonephritis that is the major cause of death (Theofilopoulos, A. N., et al., "Adv. Immunol.", 37, 269, 1985; Cohen, P. L., et al., "Annu. Rev. Immunol.", 9, 243, 1991).

At 7 weeks of age, mice were treated twice a week with 1 mg of D-PAM, L-PAM or placebo (as positive control) administered intraperitoneally. The treatment was stopped at 30 weeks of age. Mice were observed daily for clinical signs of disease and for mortality and were bled every 2 weeks for determination of anti-DNA antibody production, while urine protein levels were determined on samples taken twice a week.

Standard ELISA assay to measure the serum levels of anti-DNA antibodies was performed as follow. Microtiter plates (Costar, Cat. No 3590) were coated with a 10 µg/ml DNA (Sigma Cat. No D-8899) solution (100 µl/well) in 0.01 M phosphate buffer (pH 8.0) and incubated over night at 4° C. After washing the microtiter plates ten times with a 50 mM phosphate, 150 mM NaCl pH 7.2 buffer (PBS) containing 0.05% Tween (PBS-T), the wells were saturated with 200 µl of PBS-T containing fetal calf serum (1%) heat-inactivated 1 hour at 56° C. (PBS-T-FCS), and incubated for 2 hours at room temperature, to block the uncoated plastic surface. Plates were then washed again with PBS-T, and filled with samples (100 µl/well) previously diluted with PBS-T-FCS. After incubation for 2 hours at room temperature and subsequent washing, wells were filled with 100 µl of horseradish peroxidase labeled goat anti-mouse polyvalent immunoglobulins (IgG, IgA, IgM) (Sigma, Cat. No A-0412) solution diluted 1000 fold with PBS-T-FCS. The plates were then left to stand for 1 hour at room temperature, washed ten times and then filled with 150 µl of ophenylenediamine dihydrochloride (Sigma Cat. No P-6912) chromogenic substrate solution freshly prepared according to protocols from the manufacturer. The color was allowed to develop for 30' and the adsorbance at 450 nm were determined with an ELISA plate reader (Labsystems Multiskan Bichromatic). The results are shown in Table 3.

TABLE 3

| | Ig Anti-DNA titer (O.D.) fold increase | | | | |
|---|---|---|---|---|---|
| | Time (weeks) | | | | |
| Peptides | 8 | 10 | 14 | 16 | 18 |
| Placebo | 1.8 | 2.5 | 3.8 | 4.0 | 4.8 |
| L-PAM | 1.8 | 2.5 | 3.6 | 3.6 | 4.5 |
| D-PAM | 1.8 | 2.5 | 3.5 | 3.5 | 4.3 |

Data reported in Table 3 show that antibody anti-DNA production levels of treated groups did not differ from control group.

Urine protein levels were determined by colorimetric analysis using dipsticks (Combur 7, Boehringer Mannheim, n. cat. 185515) according to protocols from the manufacturer (Wang et al., "Proc. Natl. Acad. Sci. USA", 93, 8563–8568, 1996). The results are shown in Table 4.

TABLE 4

| | Mice with proteinuria level >1 g/L (%) | | | | |
|---|---|---|---|---|---|
| | Time (weeks) | | | | |
| Peptides | 8 | 13 | 18 | 23 | 28 |
| Placebo | 0 | 10 | 20 | 70 | 90 |
| L-PAM | 0 | 0 | 10 | 50 | 60 |
| D-PAM | 0 | 0 | 0 | 20 | 30 |

Data reported in Table 4 show that a marked delay in the onset of severe proteinuria was achieved in animals treated with L-PAM and D-PAM in comparison with untreated animals. Whereas 90% of control mice had developed proteinuria, D-PAM peptide-treated mice did not develop proteinuria until 20 weeks, and a significant percentage of these mice maintained normal renal function without evidence of proteinuria throughout the treatment period.

Coincident with ameliorating the clinical signs of severe immune complex nephritis, a dramatic prolongation of survival was observed. The results are shown in Table 5.

TABLE 5

| | Survival rate (%) | | | |
| --- | --- | --- | --- | --- |
| | Time (weeks) | | | |
| Peptides | 15 | 20 | 25 | 30 |
| Placebo | 100 | 90 | 60 | 10 |
| L-PAM | 100 | 90 | 50 | 40 |
| D-PAM | 100 | 100 | 90 | 80 |

Data reported in Table 5 show that 80% of D-PAM treated mice were still alive after 30 weeks, while only 10% of animals treated with placebo were still alive.

Further, histopathologic examination was performed on renal tissue from animal treated with D-PAM, L-PAM, or placebo. The kidneys from euthanized animals were fixed in 10% buffered formalin, and tissues were then processed and embedded in paraffin blocks. Tissue sections of about 5 μm thickness were obtained from each block, stained with hematoxylin and eosin before being examined at the light microscope. Treatment with L-PAM and D-PAM induced an evident reduction in the glomerulonephropathic progression, in comparison to the positive control group.

What is claimed is:

1. A method for treating a patient suffering from Systemic Lupus Erythematosus, said method comprising administering to a patient in need thereof an effective amount of a peptide compound of formula $$(H_2N-X_1-Thr-X_2-CO)_n-R \qquad (I)$$

wherein:
  $X_1$ and $X_2$ are each an amino acid residue selected from the group consisting of tyrosine and arginine, in L or D configuration;
  $X_1$ and $X_2$ are different from each other;
  n is 2, 3, or 4; and
  R is a group able to form a dimeric, trimeric, or tetrameric peptide.

2. The method of claim 1, wherein in said peptide compound the hydroxy group of said threonine residue is protected with a hydroxyl protecting group.

3. The method of claim 2, wherein said hydroxyl protecting group is selected from the group consisting of tert-butyl and benzyl.

4. The method of claim 1, wherein in said peptide compound the hydroxy group of said tyrosine residue is protected with a hydroxyl protecting group.

5. The method of claim 4, wherein said hydroxyl protecting group is selected from the group consisting of tert-butyl and benzyl.

6. The method of claim 1, wherein in said peptide compound the guanidine moiety of said arginine residue is protected with a guanidine protecting group.

7. The method of claim 6, wherein said guanidine protecting group is selected from the group consisting of 2,2,5,7,8-pentamethylcroman-6-sulphonyl and 4-methoxy-2,3,6-trimethylbenzene.

8. The method of claim 1, wherein in said peptide compound the hydroxy group of said threonine residue and the hydroxy group of said tyrosine residue are each protected with a hydroxyl protecting group and the guanidine moiety of said arginine residue is protected with a guanidine protecting group.

9. The method of claim 8, wherein said hydroxyl protecting group is selected from the group consisting of tert-butyl and benzyl and said guanidine protecting group is selected from the group consisting of 2,2,5,7,8-pentamethylcroman-6-sulphonyl and 4-methoxy-2,3,6-trimethylbenzene.

10. The method of claim 1, wherein in said peptide compound n is 4.

11. The method of claim 10, wherein in said peptide compound the hydroxy group of said threonine residue is protected with a hydroxyl protecting group.

12. The method of claim 11, wherein said hydroxyl protecting group is selected from the group consisting of tert-butyl and benzyl.

13. The method of claim 10, wherein in said peptide compound the hydroxy group of said tyrosine residue is protected with a hydroxyl protecting group.

14. The method of claim 13, wherein said hydroxyl protecting group is selected from the group consisting of tert-butyl and benzyl.

15. The method of claim 10, wherein in said peptide compound the guanidine moiety of said arginine residue is protected with a guanidine protecting group.

16. The method of claim 15, wherein said guanidine protecting group is selected from the group consisting of 2,2,5,7,8-pentamethylcroman-6-sulphonyl and 4-methoxy-2,3,6-trimethylbenzene.

17. The method of claim 10, wherein in said peptide compound the hydroxy group of said threonine residue and the hydroxy group of said tyrosine residue are each protected with a hydroxyl protecting group and the guanidine moiety of said arginine residue is protected with a guanidine protecting group.

18. The method of claim 17, wherein said hydroxyl protecting group is selected from the group consisting of tert-butyl and benzyl and said guanidine protecting group is selected from the group consisting of 2,2,5,7,8-pentamethylcroman-6-sulphonyl and 4-methoxy-2,3,6-trimethylbenzene.

19. The method of claim 11, wherein in said peptide compound n is 2 and R is a lysine residue.

20. The method of claim 11, wherein in said peptide compound n is 3 and R is a dipeptide lysil-lysine of formula Lys-Lys.

21. The method of claim 11, wherein in said peptide compound n is 4 and R is a branched tripeptide of formula Lys-Lys(∈Lys) or a branched tetrapeptide of formula Gly-Lys-Lys(∈Lys).

22. The method of claim 11, wherein in said peptide compound has the following formula $$(H_2N-X_1-Thr-X_2-CO)_4-(Lys)_2-Lys-Gly-OH \qquad (IA)$$

wherein
  $X_1$ and $X_2$ are as defined above.

23. The method of claim 22, wherein in said peptide compound the hydroxy group of said threonine residue is protected with a hydroxyl protecting group.

24. The method of claim 23, wherein said hydroxyl protecting group is selected from the group consisting of tert-butyl and benzyl.

25. The method of claim 22, wherein in said peptide compound the hydroxy group of said tyrosine residue is protected with a hydroxyl protecting group.

26. The method of claim 25, wherein said hydroxyl protecting group is selected from the group consisting of tert-butyl and benzyl.

27. The method of claim 22, wherein in said peptide compound the guanidine moiety of said arginine residue is protected with a guanidine protecting group.

28. The method of claim 27, wherein said guanidine protecting group is selected from the group consisting of 2,2,5,7,8-pentamethylcroman-6-sulphonyl and 4-methoxy-2,3,6-trimethylbenzene.

29. The method of claim 22, wherein in said peptide compound the hydroxy group of said threonine residue and the hydroxy group of said tyrosine residue are each protected with a hydroxyl protecting group and the guanidine moiety of said arginine residue is protected with a guanidine protecting group.

30. The method of claim 29, wherein said hydroxyl protecting group is selected from the group consisting of tert-butyl and benzyl and said guanidine protecting group is selected from the group consisting of 2,2,5,7,8-pentamethylcroman-6-sulphonyl and 4-methoxy-2,3,6-trimethylbenzene.

31. The method of claim 1, wherein said peptide compound is selected from the group consisting of:

$H_2N$-L-Arg(Pmc)-L-Thr(OtBu)-L-Tyr(OtBu)-CO)$_4$-(Lys)$_2$-Lys-Gly-OH;

($H_2N$-L-Arg-L-Thr-L-Tyr-CO)$_4$-(Lys)$_2$-Lys-Gly-OH;

and ($H_2N$-D-Arg-D-Thr-D-Tyr-CO)$_4$-(Lys)$_2$-Lys-Gly-OH, wherein:

Arg(Pmc) represents an arginine residue in which the guanidine group is protected with a 2,2,5,7,8-pentamethylcroman-6-sulphonyl group;

Thr(OtBu) represents a threonine residue in which the hydroxyl group is protected with a tert-butyl group; and Tyr(OtBu) represents a tyrosine residue in which the hydroxyl group is protected with a tert-butyl group.

32. The method of claim 1, wherein said peptide compound is administered in a dosage form which comprises an effective dose of at least one peptide compound of formula (I) and at least one pharmaceutically acceptable inert ingredient.

33. The method of claim 1, wherein said dosage form further comprises one or more ingredients selected from the group consisting of preservatives, stabilizers, surface-active agents, buffers, salts, emulsifying agents, sweeteners, dyes, and flavors.

34. The method of claim 1, wherein peptide compound is administered orally.

35. The method of claim 34, wherein said peptide compound is administered in a dosage selected from the group consisting of pills, capsules, cover pills, granules, solutions, and syrups.

36. The method of claim 1, wherein peptide compound is administered topically.

37. The method of claim 36, wherein said peptide compound is administered in a dosage selected from the group consisting of unguents and plasters.

38. The method of claim 1, wherein peptide compound is administered rectally.

39. The method of claim 38, wherein said peptide compound is administered in a dosage which is a suppositories.

40. The method of claim 1, wherein peptide compound is administered by injection, inhalation, or opthamically.

41. The method of claim 40, wherein said peptide compound is administered in a dosage which is a sterile solution.

42. The method of claim 1, wherein peptide compound is administered in an amount of from 1 to 200 mg/Kg/day.

43. The method of claim 1, wherein peptide compound is administered in an amount of from 2 to 50 mg/Kg/day.

* * * * *